United States Patent [19]

Bruzzese et al.

[11] Patent Number: 5,182,265

[45] Date of Patent: Jan. 26, 1993

[54] PHARMACOLOGICALLY ACTIVE PEPTIDE DERIVATIVES AND PHARMACEUTICAL PREPARATIONS CONTAINING THEM

[75] Inventors: Tiberio Bruzzese; Massimo Signorini; Carlo A. Fanciano; Roberta Termini, all of Milan, Italy

[73] Assignee: SPA Societa' Prodotti Antibiotici S.p.A., Milan, Italy

[21] Appl. No.: 562,657

[22] Filed: Aug. 3, 1990

[30] Foreign Application Priority Data

Aug. 28, 1989 [IT] Italy ................ 21567 A/89

[51] Int. Cl.$^5$ ................................ C07K 5/08
[52] U.S. Cl. ........................ 514/18; 530/331
[58] Field of Search ..................... 530/331; 514/18

[56] References Cited

U.S. PATENT DOCUMENTS

| 4,713,445 | 12/1987 | Syelke ........................ 530/330 |
| 4,780,528 | 10/1988 | Takemoto et al. ........... 530/331 |
| 4,784,988 | 11/1988 | Bruzzese et al. ............ 514/14 |

FOREIGN PATENT DOCUMENTS

| 186292 | 7/1986 | European Pat. Off. |
| 1063727 | 3/1967 | United Kingdom. |
| 1465235 | 2/1977 | United Kingdom. |

OTHER PUBLICATIONS

Babbitt et al, *Nature*, vol. 317, No. 6035, pp. 359-361, (1985).
Galpin et al, *Tetrahedron*, vol. 36, No. 15, pp. 2247-2253, (1980).
Rudinger, J., "Characteristics of the amino acids as . . ." pp. 1-7, Parsons, j., ed., University Park Press (1976).
Plattner et al. *J. Med. Chem.* 1988, 31(12):2277-2288.
Gayhoff, *Atlas of Protein Sequence and Structure*, 1972, vol. 5, pp. 96-99.

*Primary Examiner*—Howard E. Schain
*Attorney, Agent, or Firm*—Oblon, Spivak, McClelland, Maier & Neustadt

[57] ABSTRACT

Peptide derivatives and their salts with pharmaceutically acceptable acids or bases, having the general formula (I),

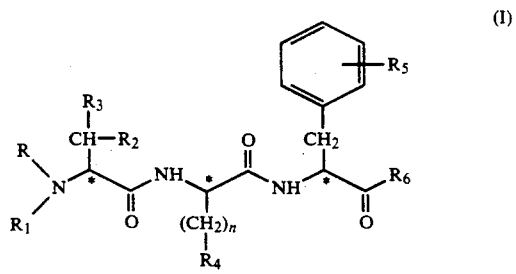

wherein
- R=—H, $C_1$-$C_3$ alkyl, $C_1$-$C_3$ acyl, alkoxycarbonyl with $C_1$-$C_4$ alkyl;
- $R_1$=—H, $C_1$-$C_3$ alkyl;
- $R_2$=—H, —OH, —OR'$_2$, wherein R'$_2$=$C_1$-$C_3$ alkyl, $C_1$-$C_3$ acyl, benzyl;
- $R_3$=—H, —CH$_3$;
- n=1,2
- $R_4$=—H, —COOH, —CONH$_2$, —COOR'$_4$, wherein R'$_4$=$C_1$-$C_3$ alkyl, benzyl;
- $R_5$=—H, 4—OH, 3,4—OH, —OR'$_5$ wherein R'$_5$=$C_1$-3 alkyl, $C_1$-$C_3$ acyl, benzyl;
- $R_6$=—OH, —NH$_2$, —OR'$_6$ wherein R'$_6$=$C_1$-$C_3$ alkyl, benzyl; endowed with analgesic, antiviral, immuno-modulating pharmacological properties, and the pharmaceutical forms containing them as active ingredients.

7 Claims, No Drawings

PHARMACOLOGICALLY ACTIVE PEPTIDE DERIVATIVES AND PHARMACEUTICAL PREPARATIONS CONTAINING THEM

The present invention relates to peptide derivatives of the general formula (I), endowed with analgesic, antiviral, immuno-modulating pharmacological properties, and to their salts at the amine or carboxylic group, providing that these groups are free, and to the pharmaceutical preparations containing them as active ingredients.

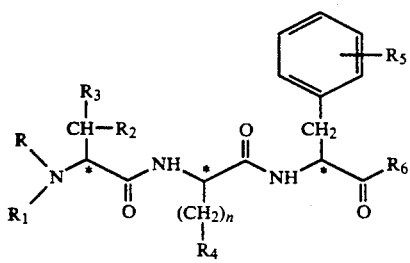
(I)

In the general formula (I) the substituents have the following meanings:

R = —H, $C_1$-$C_3$ alkyl, $C_1$-$C_3$ acyl, alkoxycarbonyl with $C_1$-$C_4$ alkyl;
$R_1$ = —H, $C_1$-$C_3$ alkyl;
$R_2$ = —H, —OH, —OR'$_2$, wherein R'$_2$ = $C_1$-$C_3$ alkyl, $C_1$-$C_3$ acyl, benzyl (Bzl);
$R_3$ = —H, —$CH_3$;
n = 1, 2
$R_4$ = —H, —COOH, —$COOH_2$, —COOR'$_4$, wherein R'$_4$ = $C_1$-$C_3$ alkyl, benzyl;
$R_5$ = —H, 4—OH, 3,4—OH, —OR'$_5$ wherein R'$_5$ = $C_1$-$C_3$ alkyl, $C_1$-$C_3$ acyl, benzyl;
$R_6$ = —OH, —$NH_2$, —OR'$_6$ wherein R'$_6$ = $C_1$-$C_3$ alkyl, benzyl.

Hence in the peptide chain of the derivatives of formula (I), the N-terminal aminoacid is:

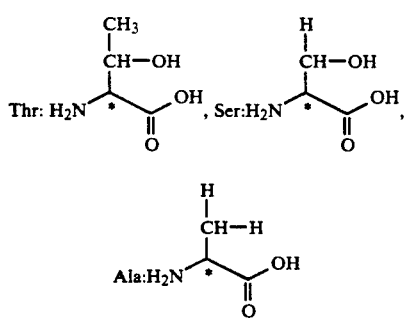

The central aminoacid is:

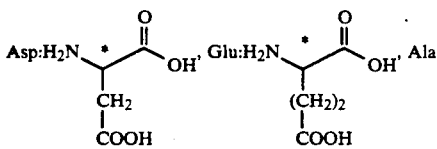

The carboxy-terminal aminoacid is:

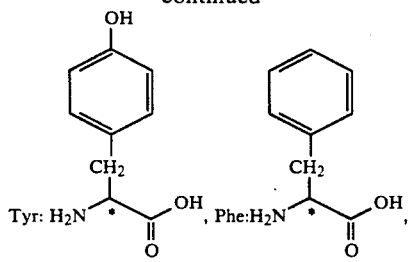

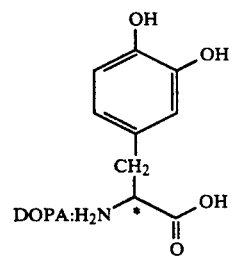

The invention relates also to derivatives wherein the hydroxy groups in Ser, Thr, Tyr and DOPA side-chain, and the carboxy groups in Asp and Glu side-chain are modified to give ether or ester derivatives and ester or primary amide derivatives, respectively, according to the above meanings of the various substituents, as well as to derivatives wherein the terminal amino group is substituted the alkyl, acyl or alkoxycarbonyl groups.

The invention relates not only to peptides of the formula (I) made of aminoacids in the "natural" L-configuration, but also to peptides where one, two or all of the three aminoacids have the "unnatural" D-configuration, or are totally or partially racemic. Hence all the possible diastereoisomers and racemates are comprised by the invention, providing that when simultaneously R = —H, $R_1$ = —H, $R_2$ = —OH, $R_3$ = —$CH_3$, n = 1, $R_4$ = —COOH, $R_5$ = 4—OH and $R_6$ = —OH, at least one of the chiral carbon atoms shown by an asterisk in formula (I) has D-configuration or is totally or partially racemic. The Italian Patent 1,190,433 (filed on Dec. 11, 1985, and granted on Feb. 16, 1988) in the applicant's name, corresponding to U.S. Pat. No. 4,784,988 (filed on Dec. 12, 1986, and granted on Nov. 15, 1988), claims the H-Thr-Asp-Tyr-OH compound comprised by the general formula (I) wherein R = —H, $R_1$ = —H, $R_2$ = —OH, $R_3$ = —$CH_3$, n = 1, $R_4$ = —COOH, $R_5$ = 4—OH, $R_6$ = —OH, but said compound has all of the three aminoacids in L-configuration. Hence all the peptide derivatives of the present invention are novel compounds.

When the nitrogen atom of the terminal amino group is basic (R and $R_1$ = —H, alkyl), the salts with pharmaceutically acceptable acids, both inorganic such as, e.g., HCl, HBr, $H_2SO_4$, $H_3PO_4$, etc, and organic such as, e.g., acetic, malonic, malic, succinic, maleic, fumaric, citric, tartaric, benzoic acid, etc. and with "acid" aminoacids such as, e.g., Asp and Glu are comprised by the invention.

When $R_3$ = —COOH and $R_5$ = —OH, the salts of the one or of the other or of both with pharmaceutically acceptable bases, both inorganic such as, e.g., sodium, potassium, ammonium, calcium, magnesium, aluminium, iron, etc. hydroxide, and organic such as, e.g., mono-, di- or trialkylamines, N-alkylethanolamines, piperidine, piperazine, N-methylglucamine, tromethamine, etc. and with "basic" aminoacids such as, e.g. Lys and Arg, are comprised by the invention.

The preparation of the peptide derivatives (I) is carried out according to methods well known in the peptide synthesis field, both in liquid and solid phase. According to the liquid phase methods, the three aminoacids are serially condensed in a suitable solvent such as DMF (N,N-dimethylformamide), THF (tetrahydrofuran) or chlorinated solvents, with subsequent formation of the two peptide bonds. The chain is formed starting from the N-terminal or, preferably, the carboxy-terminal aminoacid, wherein the carboxy group is suitably protected, e.g. as ester. The amino groups which must not to be involved by the two subsequent condensation steps, are protected by protecting groups such as, e.g., terbutyloxycarbonyl (Boc), benzyloxycarbonyl (Z), fluorenylmethoxycarbonyl (FMOC), triphenylmethyl, tosyl, formyl, phthaloyl groups, etc. The protecting groups are then selectively removed at the right moment of the synthesis, according to methods specific for the different groups and well known in the art. For avoiding undesired side-reactions, when the compounds of general formula (I) have free —OH and/or —COOH groups, such groups are preferably protected in the respective starting aminoacids by protecting groups which are then removed at the end of the peptide chain formation. The hydroxy groups are preferably protected by esterification or etherification (particularly benzyl-etherification), the carboxy groups by esterification with alcohols (particularly benzyl alcohol). If the final products of general formula (I) have substituted hydroxy and/or carboxy groups, the respective substituents are preferably inserted in the corresponding aminoacid before the peptide chain formation, so that further protective groups are not requested. Anyhow substitution reactions on free hydroxy and/or carboxy groups of final product (I) are also possible to carry on.

The peptide bond formation occurs according to methods known per se such as, e.g. by reacting the amino group with a mixed anhydride, which is prepared in situ by employing an alkyl (e.g. ethyl or isobutyl) chlorocarbonate, or by reacting the amino group with an active derivative of the carboxyl such as, e.g. an acyl chloride, a N-hydroxysuccinimide ester; a mono- or di-nitrophenyl or penta-halophenyl ester, or with an imidazolide prepared from carbonyldiimidazole. Another advantageous method consists in the direct formation of the peptide bond between the amino group and the carboxy group by means of a carbodiimide, e.g. dicyclohexylcarbodiimide, with or without the contemporary use of adjuvants such as N-hydroxybenzotriazole (HOBT) or dimethlaminopyridine (DMAP). The reactions are carried out in THF, DMF or chlorinated solvents, at temperatures ranging from −20° C. and +60° C., preferably between +4° C. and +30° C.

A particularly advantageous way for carrying out the synthesis of the peptide derivatives (I), wherein the hydroxy and carboxy groups are free and the amino group is primary, is shown by the following scheme:

1) Boc—NH—*—COOH +
   |
   (CH$_2$)$_n$
   |
   R$_4$ (II)

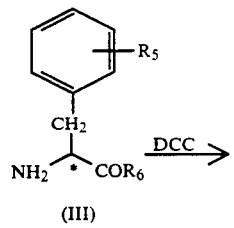

(III)

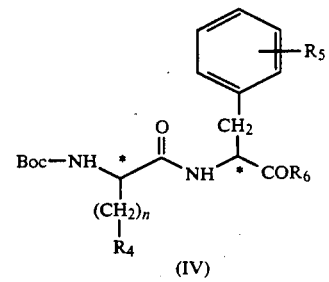

(IV)

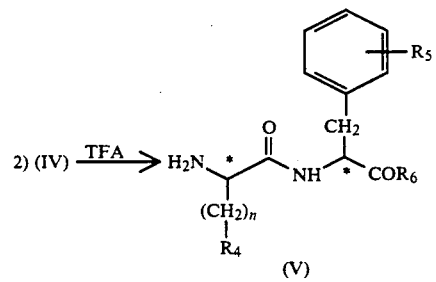

(V)

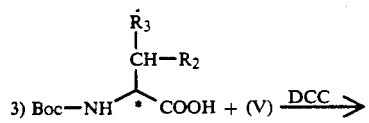

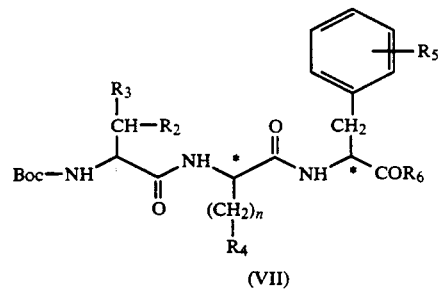

(VII)

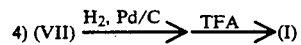

In step 1), a suitable N-Boc-protected derivative (II) of the central aminoacid (Asp, Glu, Ala) and a derivative (III) of the carboxy-terminal aminoacid (Tyr, Phe, DOPA) are reacted in methylene chloride in the presence of DCC (dicyclohexylcarbodiimide) for 1 hour at room temperature, and for one night at +4° C. After eliminating dicyclohexylurea and isolating the dipeptide derivative (IV), the Boc-protection of the amine nitrogen is removed by reacting it for 1 hour with 50% TFA (trifluoroacetic acid) in methylene chloride (step 2). In step 3), the N-deprotected dipeptide derivative (V) is condensed with a suitable derivative (VI) of the Boc-protected N-terminal aminoacid in methylene chloride in the presence of DCC,, according to the same method of step 1). In the respective formulae $R_2=$—OBzl, $R_4=$—COOBzl, $R_5=$—OBzl, $R_6=$—OBzl, while the other substituents maintain the same meanings as defined above.

The transformation of the tripeptides (VII) into the final products of formula (I) having free hydroxy and carboxy groups (step 4) takes place through subsequent catalytic hydrogenation with 10% Pd on charcoal in aqueous acetic acid (transformation of the benzylethers and benzylesters present into free hydroxy and carboxy groups) and treatment with 50% TFA in methylene chloride for about 1 hour (N-Boc-deprotection). The sequence according to which the two deprotections are carried out is not important for the yield and the purity of the final product (I). Alternatively, the transformation of (VII) into (I) is carried out in a single step by treating (VII) with gaseous 2–4N HBr in glacial acetic acid for 15–180 minutes at a temperature of 0°–80° C. (preferably with 2N HBr for 30 minutes at 20° C.). By deprotonation with a base (e.g. triethylamine), derivatives (I) having the terminal amino group free, are finally obtained as white powders. The derivatives (I) wherein R=acyl are prepared by N-Boc-deprotecting the derivatives (VII) with 50% TFA in methylene chloride, acylating the so obtained free —NH$_2$ according to one of the known methods of acylation, and finally carrying out a catalytic debenzylation with hydrogen and Pd/C.

Alternatively, the peptides (I) of the invention are prepared by means of sequential reactions in solid phase (Merrifield method). A typical route of synthesis implies the esterification of a styrene-divinylbenzene chloromethylated copolymer (Merrified resin, 1% cross-linked) with the carboxy-terminal aminoacid having the amino group (e.g. as Boc) and, if present, the phenolic hydroxy groups of the side-chain (e.g. as benzylesters) suitably protected. After isolating Boc-protected aminoacid-resin compound and determining the degree of esterification (mmol of aminoacid/g of resin), the N-protecting group is removed according to known methods, e.g. by reaction with trifluoroacetic acid. After treating with triethylamine, the condensations of the central and N-terminal aminoacid, both being N-Boc-protected and having the carboxy and hydroxy groups (when present in the side-chain) protected as benzylesters and benzylethers, respectively, are sequentially carried out according to the same procedure (condensation with DCC). The O-benzyl-protected N-Boc-tripeptide-resin compound is so obtained. The cleavage from the resin and the N,O-deprotections are carried out according to known methods such as, e.g. treatment with gaseous HBr in TFA in the presence of anisole, or with liquid dry HF. After the deprotonation of the amino group by means of a base and the suitable isolation and purification steps, the product of formula (I) is obtained as white powder. Optional substituents at amino and/or hydroxy and carboxy groups are inserted, according to the general formula (I), into the relevant aminoacids before the peptide condensation reactions, or in some cases, they are inserted at the end when the peptide chain has been already formed.

From the products (I) of the invention salts at the amine (when R and $R_1=$—H, alkyl) or at the carboxy (when it is free) groups are prepared by treatment with equivalent amounts of acids or, respectively, bases in aqueous or organic solution. The salts are obtained from the solutions thereof by concentrating and/or cooling, evaporation to dryness, freeze-drying, spray-drying, precipitation by solvents, etc.

In view of the analgesic and also antiviral and immuno-modulating activities, the compounds (I) are suitable for human and veterinary therapeutic. In the human therapy, a dosage from 100 to 1000 mg/day, preferably from 200 to 600 mg/day, is administered in a single dose or in a subdivided dose during 24 hours.

The compounds (I) are formulated into different known pharmaceutical preparations such as, e.g. soft or hard gelatine capsules, tablets, sugar-coated pills, sustained release capsules or tablets, monodose oral envelopes or ampuls instantaneous syrup granulates, syrups, solutions for injection, freeze-dried powders for injection, suppositories, creams, etc. Depending on the different formulations, together with the active ingredient suitable adjuvants are employed such as eccipients, stabilizers, solvents, dyeing, flavouring, sweetening agents, etc. as commonly made in the pharmaceutical technology.

The following Examples illustrate but do not limit anyway the invention.

EXAMPLE 1

Liquid phase synthesis of H-Thr-Asp-D-Tyr-OH

A) 14 g of H-D-Tyr(Bzl)-OBzl (38.7 mmoles) and 12.53 g of Boc-Asp(OBzl)-OH (38.7 mmoles) are dissolved in 145 ml of CH$_2$Cl$_2$. In the ice-cooled solution 8.78 g of DCC (42.5 mmoles) dissolved in 35 ml of CH$_2$Cl$_2$ are dropped. The mixture is left under stirring for 1 h at room temperature and for one night at 4° C. The resulting precipitate (dicyclohexylurea) is filtered off and the filtrate is evaporated to dryness under vacuum. The semi-solid residue is taken up with 170 ml of 70/30 ethanol/H$_2$O, the mixture is refluxed while two immiscible phases are formed, and left to cool under vigorous stirring. The resulting white solid is filtered and treated again with 70/30 ethanol/H$_2$O to reflux. Thus 20 g of Boc-Asp(OBzl)-D-Tyr(Bzl)-OBzl are obtained.

m.p.=67° C.; $[\alpha]_D^{25}=+4.3°$ (C=1, CH$_2$Cl$_2$)

B) 20 g of the previous product (30 mmoles) are dissolved in 60 ml of trifluoroacetic acid (TFA)/CH$_2$Cl$_2$ 1/1, and kept under stirring for 1 h at room temperature. The solution is evaporated under vacuum and the thick oily residue is treated with dry ether thus obtaining a white precipitate which is filtered and washed with dry ether. Hence 18 g of TFA H-Asp-(OBzl)-D-Tyr(Bzl)-OBzl are obtained.

m.p.=125°–8° C.; $[\alpha]_D^{25}=+1.6°$ (C=1, THF)

C) 17.45 g of the previous product (25.6 mmoles) are suspended in 65 ml of CH$_2$Cl$_2$, and 3.6 ml of triethylamine (25.6 mmoles) are added therein. The clear solution so obtained is ice-cooled and added with 7.9 g of Boc-Thr(Bzl)-OH (25.6 mmoles) dissolved in 37 ml of CH$_2$Cl$_2$ followed by 5.81 g of DCC (28.2 mmoles) dissolved in 28 ml of CH$_2$Cl$_2$ and slowly dropped. The mixture is kept under stirring for 1 h at room temperature and for one night at 4° C. The white precipitate of dicyclohexylurea is filtered off, and the filtrate is evaporated to dryness under vacuum. The thick oily residue is purified by refluxing with 100 ml of 70/30 ethanol/H$_2$O and slowly cooling the mixture of two immiscible liquid phase so obtained while vigorously stirring. After a second similar treatment, 20 g of Boc-Thr(Bzl)-Asp(OBzl)-D-Tyr(Bzl)-OBzl (23.3 mmoles) are obtained as white powder. (Product of formula (I), wherein R=Boc, $R_1$=—H, $R_2$=-OBzl, $R_3$=—CH$_3$, n=1, $R_4$=—COOBzl, $R_5$=4—OBzl, $R_6$=—OBzl)

m.p.=80° C.; $[\alpha]_D^{25}$=+2° (c=1, CH$_2$Cl$_2$).

D) 20 g of the previous product (23.3 mmoles) are dissolved in 150 ml of 80% acetic acid, 5 g of 10% Pd on charcoal are added and the mixture is hydrogenated at room pressure and temperature for 22 hours. The catalyst is filtered off and the solvent is evaporated under vacuum. The solid residue (11 g) is Boc-Thr-Asp-D-Tyr-OH (formula (I), wherein R=Boc, $R_1$=H, $R_2$=—OH, $R_3$=—CH$_3$, n=1, $R_4$=—COOH, $R_5$=—4—OH, $R_6$=—OH). This is dissolved as such in 100 ml of TFA/CH$_2$Cl$_2$ 1/1 and kept at room temperature for 90 minutes. After evaporation to dryness, the semi-solid residue is taken up with 80 ml of ethyl ether, and the resulting solid is filtered so obtaining 10 g of TFA.H-Thr-Asp-D-Tyr-OH.

m.p.=110° C., $[\alpha]_D^{25}$=−29.5 (C=1, THF).

E) 10 g of the previous product (19.6 mmoles) are dissolved in 50 ml of absolute ethanol. The solution is cooled in ice bath, and 2.84 ml of triethylamine (20 mmoles) in 10 ml of ethanol are slowly dropped therein under stirring. A fine white precipitate rapidly results, which is filtered and accurately slurried twice in 30 ml of cold ethanol. After drying under vacuum at 40° C., 7 g of H-Thr-Asp-D-Tyr-OH (17.6 mmoles) are obtained. (Product of formula (I) wherein R=—H, $R_1$=—OH, $R_3$=—CH$_3$, n=1, $R_4$=—COOH, $R_5$=4—OH, $R_6$=—OH). m.p.=138° C.; $[\alpha]_D^{25}$=−25.7° (C=1, H$_2$O); Rf=0.41 (silica gel plates F$_{254}$. Eluant: CH$_3$OH/CH$_3$Cl/NH$_4$OH conc. 40/40/14. Detection: UV 254 nm, or spray with ninhydrin). DereThe aminoacid analysis confirms the product structure.

EXAMPLE 2

According to the method of Example 1, by condensing H-Tyr(Bzl)-OBzl, Boc-Asp(OBzl)-OH and Boc-Thr(Bzl)-OH having suitable L, D or DL chirality, the following tripeptides are prepared:

| | |
|---|---|
| H—Thr—D—Asp—Tyr—OH | $[\alpha]_D^{25}$ = +34.5° (C = 1, H$_2$O) M.P. 160° C. |
| | Rf = 0.44 (CHCl$_3$/CH$_3$OH/NH$_4$OH conc. 40/40/14) |
| H—D—Thr—Asp—Tyr—OH | $[\alpha]_D^{25}$ = −1.25°(C = 1, H$_2$O) M.P. 149° C. |
| | Rf = 0.5 (CHCl$_3$/CH$_3$OH/NH$_4$OH conc. 40/40/14) |
| H—D—Thr—D—Asp—Tyr—OH | $[\alpha]_D^{25}$ = +19.6° (C = 1, H$_2$O) M.P. 95° C. |
| | Rf = 0.42 (CHCl$_3$/CH$_3$OH/NH$_4$OH conc. 40/40/14) |
| H—Thr—D—Asp—D—Tyr—OH | $[\alpha]_D^{25}$ = +8 (C = 1, H$_2$O) M.P. = 120° C. |
| | Rf = 0.41 (CHCl$_3$/CH$_3$OH/NH$_4$OH conc. 40/40/14) |
| H—D—Thr—Asp—D—Tyr—OH | $[\alpha]_D^{25}$ = −23.2 (C = 1, H$_2$O) M.P. 140° C. |
| | Rf = 0.39 (CHCl$_3$/CH$_3$OH/NH$_4$OH conc. 40/40/14) |
| H—D—Thr—D—Asp—D—Tyr—OH | $[\alpha]_D^{25}$ = −8.2° (C = 1, H$_2$O) M.P. = 148° C. |
| | Rf = 0.40 (CHCl$_3$/CH$_3$OH/NH$_4$OH conc. 40/40/14) |
| H—DL—Thr—Asp—Tyr—OH | $[\alpha]_D^{25}$ = +3 (C = 1, H$_2$O) M.P. = 135° C. |
| | Rf = 0.40 (CHCl$_3$/CH$_3$OH/NH$_4$OH conc. 40/40/14) |
| H—Thr—Asp—D,L—Tyr—OH | $[\alpha]_D^{25}$ = +12.5 (C = 1, H$_2$O) M.P. = 193-5°C. |
| | Rf = 0.34 (CHCl$_3$/CH$_3$OH/NH$_4$OH conc. 40/40/14) |

EXAMPLE 3

Liquid phase synthesis of Ac-Thr-Asp-Tyr-OH 4 g of Boc-Thr(Bzl)-Asp(OBzl)Tyr(Bzl)-OBzl (4.6 mmoles), prepared from H-Tyr(Bzl)-OBzl, Boc-Asp(OBzl)-OH and Boc-Thr-(Bzl)-OH according to the method of Example 1, A)-C), are dissolved in 40 ml of TFA/CH$_2$Cl$_2$ 1/1 and kept under stirring at room temperature for 1 hour. The solvent is evaporated under vacuum and the thick oily residue is taken up with ethyl ether, whereby a white solid is obtained which is filtered and dried under vacuum. The so obtained 3.5 g of TFA.H-Thr-(Bzl)-Asp(OBzl)-Tyr(Bzl)-OBzl (4.01 mmoles) are suspended in 30 ml of CH$_2$Cl$_2$ and treated with 0.56 ml of triethylamine (4.01 mmoles) dissolved in 5 ml of CH$_2$Cl$_2$. The resulting clear solution is cooled in ice and added with 0.277 g of acetic acid (4.6 mmoles). Finally a solution of 0.91 g of DCC (4.4 mmoles) in 10 ml of CH$_2$Cl$_2$ is slowly dropped therein under stirring.

The mixture is kept at room temperature for 24 hours and at reflux temperature for 2 hours.

The mixture is cooled, the resulting dicyclohexylurea is filtered off and the filtrate is evaporated to dryness under vacuum. The semi-solid residue (3.8 g) is dissolved in 80% acetic acid and hydrogenated for 16 hours at room pressure and temperature in the presence of 0.95 g of 10% Pd on charcoal. The catalyst is filtered off, the filtrate is evaporated to dryness under vacuum and taken up with 30 ml of ethyl ether, whereby the rapid formation of a white solid is obtained that is filtered and washed several times with ether. After drying, 1.6 g of Ac-Thr-Asp-Tyr-OH (3.6 mmoles) are obtained. (Product of formula (I), wherein R=—COCH$_3$, $R_1$=—H, $R_2$=—OH, $R_3$=—CH$_3$, n=1, $R_4$=—COOH, $R_5$=4—OH, $R_6$=—OH).

m.p.=66°-7° C.; $[\alpha]_D^{25}$=-19.9) (C=1, H$_2$O).

EXAMPLE 4

Solid phase synthesis of H-Thr-Asp-D-Tyr-OH

A) 7,5 g of a chloromethylated styrene-divinylbenzene copolymer (Merrifield resin, 1% cross-linked) are esterified with 1.113 g of Boc-D-Tyr(Bzl)-OH (3 mmoles) by refluxing for 45 hours in 60 ml of ethyl acetate in the presence of 0.42 ml of triethylamine. The resin is separated by filtration, washed successively with ethyl acetate, ethanol and water, and dried under vacuum at 25° C. 8.09 g of Boc-D-Tyr(Bzl)-resin are obtained having an esterification degree of 0.201 mmoles of D-Tyr/g calculated on the basis of the difference between the total amount of D-Tyr derivative employed and the one remained in mother liquors and in washings (determination by UV at 276 nm). The resin is Boc-deprotected by treatment with 70 ml of TFA/CH$_2$Cl$_2$ 1/1 for 30 minutes at room temperature; thereafter it is filtered and suspended for 30 minutes under stirring in 70 ml of 10% triethylamine in chloroform. After filtrating, washing with chloroform and drying under vacuum, the product H-D-Tyr(Bzl)-resin is obtained.

B) The previous step product is suspended in 190 ml of CH$_2$Cl$_2$ and treated with 1.575 g of Boc-Asp(OBzl)-OH (4.86 mmoles, three times the stoichiometric amount). After short stirring, 1.005 g of DDC (4.867 mmoles) dissolved in 40 ml of $CH_2Cl_2$ is added therein, and the reaction is left to proceed for 12 h at room temperature under stirring. At the end, the resin is filtered, washed with $CH_2Cl_2$ and $CH_3OH$ and dried. After checking the completion of the reaction by ninhydrin reaction (no colour due to unreacted amino groups), the resin is Boc-deprotected (TFA) and treated with $Et_3N$ as described in A), whereby the product Boc-Asp(OBzl)-D-Tyr(Bzl)-resin is obtained.

C) The previous step product is reacted with Boc-Thr-(Bzl)-OH and DCC in $CH_2Cl_2$ according to the same method as described in B). After filtration, washing with $CH_2Cl_2$ and $CH_3OH$ and drying, the product Boc-Thr(Bzl)-Asp(OBzl)-D-Tyr-(Bzl)-resin is obtained.

D) The cleavage of the peptide chain from the resin and the simultaneous deprotection of the protected amino, carboxy and hydroxy groups are carried out by suspending the resin obtained from the previous step in 120 ml of TFA containing 6 ml of anisole, cooling the suspension under stirring at 10°-15° C., and bubbling therein a stream of gaseous HBr at the same temperature for 80 minutes. At the end the spent resin is separated by filtration and washed with TFA. The combined filtrate and washings are evaporated to dryness under vacuum. Thereby 0.766 g of deprotected tripeptide are obtained in form of trifluoroacetate (1.5 mmoles) which are dissolved in 35 ml of ethanol/ethyl acetate 1/1 and added with 0.22 ml of $Et_3N$ (1.6 mmoles). By cooling at 0° C. a white powder precipitates from the solution, and is then filtered, washed with ethanol and dried. Thereby 0.556 g (1.4 mmoles) of H-Thr-Asp-D-Tyr-OH are obtained. The aminoacid analysis and the physico-chemical properties (m.p., $[\alpha]_D^{25}$, Rf) confirm the identity of this product with H-Thr-Asp-D-Tyr-OH prepared by synthesis in liquid phase (see Example 1).

EXAMPLE 5

According to the method of peptide synthesis in liquid phase shown in Example 1, tripeptide compounds are prepared by sequentially condensing (by DCC) the suitably protected derivatives of three aminoacids among which the carboxy-terminal one is Tyr or Phe, the central one is Asp, Glu or Ala, and the N-terminal one is Ser, Thr or Ala. The carboxy-terminal aminoacid has the carboxy group protected as benzylester, the central aminoacid is N-Boc-protected, and the Boc-protection is selectively removed (TFA) before the condensation with the N-terminal aminoacid that is also N-Boc-protected. Hydroxy groups possibly present in the side-chains are protected as benzylethers, and carboxy groups in the side-chains are protected as benzylesters. The final deprotections yielding the free tripeptide are carried out according to the methods of Example 1. The starting protected aminoacid derivatives are commercial products or synthetized according to methods known in the art. By this way the following tripeptides are prepared:

H-Ser-Asp-Tyr-OH

Product of formula (I) wherein $R=R_1=—H$, $R_2=—OH$, $R_3=—H$, $n=1$, $R_4=—COOH$, $R_5=4—OH$, $R_6=—OH$)
MP=174°-8° C.; $[\alpha]_D^{25}=+6.7°$; Rf=0.33

H-Thr-Glu-Tyr-OH

Product of formula (I) wherein $R=R_1=—H$, $R_2=—OH$, $R_3=—CH_3$, $n=2$, $R_4=—COOH$, $R_5=4—OH$, $R_6=—OH$)
MP=107°-10° C.; $[\alpha]_D^{25}=+5.5°$; Rf=0.31

H-Ala-Asp-Tyr-OH

Product of formula (I) wherein $R=R_1=—H$, $R_2=R_3=—H$, $n=1$, $R_4=—COOH$, $R_5=4—OH$, $R_6=—OH$)
MP=169°-73° C.; $[\alpha]_D^{25}=+4.6°$; Rf=0.35

H-Thr-Ala-Tyr-OH

Product of formula (I) wherein $R=R_1=—H$, $R_2=—OH$, $R_3=—CH_3$, $n=1$, $R_4=—H$, $R_5=4—OH$, $R_6=—OH$)
MP=145°-9° C.; $[\alpha]_D^{25}=+3.3°$; Rf=0.36

H-Thr-Asp-Phe-OH

Product of formula (I) wherein $R=R_1=—H$, $R_2=—OH$, $R_3=—CH_3$, $n=1$, $R_4=—COOH$, $R_5=—H$, $R_6=OH$)
MP=188°-90° C. (dec.); $[\alpha]_D^{25}=+7.8$; Rf=0.38

The $[\alpha]_D^{25}$ values are determined in aqueous solution; the Rf values are determined from TLC on silica gel by eluting with $CH_3OH/CH_2Cl_2/NH_4OH$ conc. 40/40/14 and detecting the spots under UV light (254 nm) or spraying with ninhydrin (yellow colour).

EXAMPLE 6

According to the methods of Example 5 and starting from H-Tyr(Bzl)-OBzl, Boc-DL-Glu(OBzl)-OH and Boc-Thr(Bzl)-OH, the tripeptide H-Thr-DL-Glu-Tyr-OH is prepared.

EXAMPLE 7

According to a method similar to the one in Example 5, H-Thr-Asp-DOPA is prepared by sequentially condensing the relevant aminoacids suitable protected. Due to the ready oxidability of DOPA and the derivatives thereof, all the preparation steps are carried out in inert atmosphere. Equimolar amounts of Boc-Asp(OBzl)-OH and 3,4-diacethoxyphenylalanine methyl ester (prepared according to J. Med. Chem., 20, 1435, 1977) are condensed by DCC in $CH_2Cl_2$. The protected dipeptide so obtained is N-Boc-deprotected (TFA/$CH_2Cl_2$ 1/1) and condensed (DCC) with an equimolar amount of Boc-Thr(Bzl)-OH The protected tripeptide so prepared is catalitically hydrogenated (10% Pd/C in 50% aqueous acetic acid). The operative conditions yield, beside the cleavage of the benzyl protective groups, the hydrolysis of the acetyl and methyl ester groups in DOPA. So Boc-Thr-Asp-DOPA is obtained which yields H-Thr-Asp-DOPA hydrochloride by deprotection with TFA/$CH_2Cl_2$, evaporation to dryness and repeated evaporations to dryness with methanol containing gaseous HCl (Product of formula (I) with $R=R_1=—H$, $R_2=—OH$, $R_3=—CH_3$, $n=1$, $R_4=—COOH$, $R_5=—3,4—OH$, $R_6=—OH$).
$[\alpha]_D^{25}=+5.3$ (C=1, $CH_3OH$); m.p.=106°-8° C.; Rf=0.37 ($CH_2Cl_2/CH_3OH$ 1/1).

EXAMPLE 8

According to the methods of Example 5 and starting from aminoacids whose carboxy and amino groups have been modified in the beginning, the following derivatives of formula (I) are prepared, bearing correspondingly modified carboxy and amino groups H-Thr-Asp(OMe)-Tyr-OH Product of formula (I) wherein $R=R_1=-H$, $R_2=-OH$, $R_3=-CH_3$, $n=1$, $R_4=-COOCH_3$, $R_5=4-OH$, $R_6=-OH$)
$MP=100°-5°$ C. $[\alpha]_D^{25}=+4.4$ Rf=0.58

H-Thr-Asp-Tyr-OMe

Product of formula (I) wherein $R=R_1=-H$, $R_2=-OH$, $R_3=-CH_3$, $n=1$, $R_4=-COOH$, $R_5=4-OH$, $R_6=-OCH_3$)
$MP=100°-3°$ C. $[\alpha]_D^{25}=+14.6$ Rf=0.66

Boc-Thr-Asp-Tyr-OH

Product of formula (I) wherein $R=-H$, $R_1=t$ Bu OCO—, $R_2=-OH$, $R_3=-CH_3$, $n=1$, $R_4=-COOH$, $R_5=4-OH$, $R_6=-OH$)
$MP=185°-90°$ C. $[\alpha]_D^{25}=+24.9$ Rf=0.55

Me$_2$-Thr-Asp-Tyr-OH.CH$_3$COOH.

Product of formula (I) wherein $R=R_1=-CH_3$, $R_2=-OH$, $R_3=-CH_3$, $n=1$, $R_4=-COOH$, $R_5=4-OH$, $R_6=-OH$)
$MP=157°-60°$ C. $[\alpha]_D^{25}=+9.97$ Rf=0.51

The rotatory powers are determined in aqueous solution (C=1), and TLCs are carried out on silicagel plates by eluting with CHCl$_3$/CH$_3$OH/NH$_4$OH conc. 40/40/14. The spots were detected under UV light (254 nm) or, for compounds having free primary amino and carboxy groups, by spraying with ninhydrin (yellow colour).

In a similar manner, H-Thr-Asp(OMe)-Tyr-OMe, H-Thr-Asp-Tyr-NH$_2$, H-Thr-Asp-Tyr(Me)-OH are prepared.

EXAMPLE 9

Synthesis of H-Thr-Asp(OMe)-D-Tyr-OMe

H-Thr-Asp-D-Tyr-OH prepared according to Example 1 is dissolved in 15 volumes of dimethylsulfoxide, the solution is cooled to 0°-5° C. and added with an excess of diazomethane in ether solution. The reaction is left for 2 hours at 0°-5° C. and for further 2 hours at room temperature. By diluting the solution with ether, a slightly pasty solid precipitates and is then filtered, stirred in a little amount of ether for half an hour, and filtered again. H-Thr-Asp(Ome)-D-Tyr-OMe is thereby obtained as a crystalline white powder.

EXAMPLE 10

H-Thr-Asp-D-Tyr-OH hydrochloride

H-Thr-Asp-D-Tyr-OH is dissolved in 5 volumes of water, and the solution is added with an equivalent amount of 1N HCl. By freeze-drying or diluting with acetone the solution, the hydrochloride is obtained as a very water soluble powder.

EXAMPLE 11

H-Thr-Asp-Tyr-OH lysine salt

H-Thr-Asp-Tyr-OH is dissolved in 5 volumes of water and an equimolar amount of lysine is dissolved in such solution.

The solution is concentrated to small volume under vacuum and added with acetone. By short cooling the lysine salt precipitates as a freely water soluble powder.

EXAMPLE 12

100 mg and 200 mg capsules for oral administration

|  | 100 mg Cps | 200 mg Cps |
|---|---|---|
| H—Thr—Asp—D—Tyr—OH | 35.000 g | 70.00 g |
| Mg stearate | 1.110 g | 2.22 g |
| Microcrystalline cellulose | 51.800 g | 103.60 g |

The mixture is subdivided into 350 capsules.

EXAMPLE 13

Sterile freeze-dried powder for 100 mg and 200 mg injectable preparation

|  | 100 mg f-d | 200 mg f-d |
|---|---|---|
| H—Thr—Asp—D—Tyr—OH | 32.500 g | 65.00 g |
| Sodium chloride | 2.280 g | 4.56 g |
| Bidistilled water to | 650 ml | 650.00 ml |

The solution is filtered on a sterilizing membrane. 325 ampuls are filled with 2 ml each of sterile solution and freeze-dried in sterile conditions.

EXAMPLE 14

200 mg suppositories

| H—Thr—Asp—D—Tyr—OH | 20 g |
|---|---|
| Fatty acids glyceride esters | 160 g |

The micronized active ingredient is dispersed in the suppository mass (fatty acids glyceride esters) melted at 42° C. The homogeneous suspension is subdivided in 100 valves for suppositories and cooled.

EXAMPLE 15

5% cream for topical application

| H—Thr—Asp—D—Tyr—OH | 17.500 g |
|---|---|
| Emulsifying agent | 14.000 g |
| Propylene glicol | 42.000 g |
| White mineral oil | 28.000 g |
| Lanolin | 35.000 g |
| Preservative agent (Paraben) | 0.525 g |
| Citric acid · H$_2$O | 0.945 g |
| Sodium citrate · 2H$_2$O | 0.980 g |
| Distilled water | 211.050 g |

The cream obtained with the above-mentioned components is packed in 15 g tubes.

We claim:
1. A peptide selected from the group consisting of:

H-Thr-Asp-Phe-OH

H-D-Thr-Asp-Tyr-OH

H-Thr-Asp-D-Tyr-OH

H-Ala-Asp-Tyr-OH and pharmaceutically acceptable salts thereof.

2. The peptide of claim 1 which is:

H-Thr-Asp-Phe-OH and pharmaceutically acceptable salts thereof.

3. The peptide of claim 1 which is:

H-D-Thr-Asp-Tyr-OH and pharmaceutically acceptable salts thereof.

4. The peptide of claim 1 which is:

H-Thr-Asp-D-Tyr-OH and pharmaceutically acceptable salts thereof.

5. The peptide of claim 1 which is:

H-Ala-Asp-Tyr-OH and pharmaceutically acceptable salts thereof.

6. A pharmaceutically formulation having analgesic activity, which comprises an effective amount of a peptide or salts thereof according to claim 1, in combination with a pharmaceutically acceptable carrier or adjuvant.

7. A pharmaceutical formulation for oral administration comprising an effective amount of a peptide or salts thereof according to claim 1, in combination with a pharmaceutically acceptable carrier or adjuvant.

* * * * *